US011051893B2

(12) United States Patent
van Dam et al.

(10) Patent No.: US 11,051,893 B2
(45) Date of Patent: Jul. 6, 2021

(54) HEART CONDITION DETERMINATION METHOD, ROBOT CONTROL AND SYSTEM

(71) Applicant: Peacs Investments B.V., Nieuwerbrug aan den Rijn (NL)

(72) Inventors: Eelco Matthias van Dam, Arnhem (NL); Peter Michael van Dam, Arnhem (NL)

(73) Assignee: Peacs Investments B.V., Nieuwerbrugaan den Rijn (NL)

( * ) Notice: Subject to any disclaimer, the term of this patent is extended or adjusted under 35 U.S.C. 154(b) by 275 days.

(21) Appl. No.: 15/770,381

(22) PCT Filed: Oct. 21, 2016

(86) PCT No.: PCT/NL2016/050728
§ 371 (c)(1),
(2) Date: Apr. 23, 2018

(87) PCT Pub. No.: WO2017/099582
PCT Pub. Date: Jun. 15, 2017

(65) Prior Publication Data
US 2019/0060006 A1    Feb. 28, 2019

(30) Foreign Application Priority Data
Oct. 21, 2015  (NL) ..................................... 2015642

(51) Int. Cl.
*A61B 5/00*    (2006.01)
*A61B 34/30*    (2016.01)
(Continued)

(52) U.S. Cl.
CPC .............. *A61B 34/30* (2016.02); *A61B 5/339* (2021.01); *A61B 5/341* (2021.01); *A61B 5/363* (2021.01);
(Continued)

(58) Field of Classification Search
CPC ... A61B 5/04011; A61B 5/044; A61B 5/0452; A61B 5/0456; A61B 5/0468; A61B 5/0472
See application file for complete search history.

(56) References Cited

U.S. PATENT DOCUMENTS

| 2011/0060234 A1 | 3/2011 | Zhou et al. |
| 2012/0059270 A1* | 3/2012 | Grunwald .............. A61B 5/042 600/509 |

(Continued)

OTHER PUBLICATIONS

Van Dam et al., "ECGSIM: Interactive Simulation of the ECG for Teaching and Research Purposes", Computing in Cardiology, 2010, pp. 841-844, vol. 37.

*Primary Examiner* — Allen Porter
(74) *Attorney, Agent, or Firm* — The Webb Law Firm

(57) ABSTRACT

A method for performing location determination of a candidate area of a heart disorder, while applying information from an ECG device and a processing unit: obtaining a torso model and/or a heart model of a subject, for the purpose of determining locations, determining of an origin in the hearts model and torso model, obtaining the location information relating to a number of ECG electrodes relative to the torso model and/or hearts model of the subject, based on the location information in the torso model and/or heart model, positioning of the number of ECG electrodes, obtaining of electrode measuring information related to respective distinct ECG electrodes, constructing weighted vector is based on electrode measuring information while applying a predetermined ECG feature, relating the weighted vectors to the origin and the respective electrodes, based on the weighted vectors relative to the said origin, constructing of an initial anatomical feature vector.

24 Claims, 14 Drawing Sheets

(51) Int. Cl.
*G16H 50/50* (2018.01)
*A61B 5/339* (2021.01)
*A61B 5/341* (2021.01)
*A61B 5/363* (2021.01)
*A61B 5/364* (2021.01)
*A61B 18/14* (2006.01)
*A61B 18/00* (2006.01)

(52) U.S. Cl.
CPC .............. *A61B 5/364* (2021.01); *A61B 5/684* (2013.01); *A61B 5/7475* (2013.01); *A61B 18/1492* (2013.01); *G16H 50/50* (2018.01); *A61B 5/0064* (2013.01); *A61B 2018/00577* (2013.01); *A61B 2018/00839* (2013.01); *A61B 2034/301* (2016.02)

(56) References Cited

U.S. PATENT DOCUMENTS

| | | |
|---|---|---|
| 2013/0060156 A1 | 3/2013 | Gregg et al. |
| 2014/0046207 A1 | 2/2014 | Saba et al. |
| 2014/0276157 A1 | 9/2014 | Macneil et al. |

\* cited by examiner

30ms

90ms

140ms

HEART CONDITION DETERMINATION METHOD, ROBOT CONTROL AND SYSTEM

CROSS-REFERENCE TO RELATED APPLICATIONS

This application is the United States national phase of International Application No. PCT/NL2016/050728 filed Oct. 21, 2016, and claims priority to Dutch Patent Application No. 2015642 filed Oct. 21, 2015, the disclosures of which are hereby incorporated in their entirety by reference.

BACKGROUND OF THE INVENTION

Field of the Invention

The present invention relates to a method of analyzing data relating to the location of an electrical this order in the heart. More specifically, the invention relates to determining an area in which the location of the disorder is located. Furthermore, the invention relates to a method for controlling the operation of a medical device according to the present invention, preferably for the purpose of performing offer a method according to the present invention. More specifically, the invention relates to determining an area in which a PVC is located. A PVC (premature ventricular contraction) is a ventricular extrasystole. The heart skips a contraction and afterwards and extra powerful contraction follows. Depending on the condition of a subject (patient) a treatment for this is required. Such a treatment relates for example to elimination of an amount of muscle tissue were the PVC initiates.

Technical Background

For the purpose of such a treatment it is preferred that the location of the PVC is known, is known as accurately as possible before beginning after the treatment in order to avoid intensive searching for the location in the body. This is a relevant advantage as searching in the body relates to an increase of risk and an extension of time for the procedure. If it would be possible to work based on data relating to the location, the average duration of a treatment is limited or the predictability of the duration of a treatment is enlarged.

The subject matter of this document is relating to the spatiality of the torso and the heart that is present therein. To this end, use is made of models thereof. These models related therefore to a hart model and a torso model. Also, use is being made of the term hart-torso model. These terms are used interchangeably and in this use substantially mean the same within the meaning of this text.

It is known in itself that a doctor can make a good estimation during an operation on the basis of a qualitative approach of the so-called vector loop relative to the heart and the person on the basis of experience and the usual position of electrodes on the torso and on the basis of a lot of experience. As such, the individual experience and aptitude of the doctor were essential. Such an approach was transferable in a time span of years in the training of doctors.

Several ways of doing analysis on the basis of data relating to the heart, such as determinations relating to the timing of excavation in the heart and relating to a determination of location of the excavation based on a fastest path algorithm of the present inventor have been known.

That method however requires a large number of measuring points and over a long period of time, such as 3-9 hours, a very large number of measurements on the basis of each of which calculations with iterations needs to be performance. Because of this, this method has appeared to be unworkable in practice of e.g. a treatment room.

SUMMARY OF THE :INVENTION

In order to provide a method for allowing a broader application, the present invention provides a method, such as implemented on a computer, for performing of a location determination for determining of a candidate area of a heart disorder, such as a PVC (premature ventricular contraction) causing part of the heart muscle, while applying information from an ECG device and a processing unit:

obtaining a torso model and or a hard model of a subject,
for the purpose of determining locations, determining of an origin in the hearts model and torso model, such as in the proximity of the center of the heart,
obtaining the location information relating to a number of ECG electrodes relative to the torso model and or hearts model of the subject,
based on the location information in the torso model and/or heart model, positioning of the number of ECG electrodes,
obtaining of electrode measuring information, such as embodied by means of electrode vector, related to respective distinct ECG electrodes,
constructing weighted, such as preferably normalized, vector is based on electrode measuring information while applying a predetermined ECG feature,
relating the weighted vectors to the origin and the respective electrodes,
based on the weighted vectors relative to the said origin, constructing of an initial anatomical feature vector determining an initial anatomical feature geography and determining a direction towards the candidate area.

An advantage of such a method according to the present invention is that this method all is possible in a very flexible manner, i.e. based on several information sources relating to a hearts torso model. Furthermore, the location information is obtainable in the application of a quite mobile device, such as a camera or camera assembly that is capable of providing three-dimensional information such that in a simple manner of the location of the used ECG electrodes can be related to the heart-torso model or can be fitted in that model. A yet further advantage of such a method is that practically usable results can be calculated immediately after obtaining the several kinds of information while applying a device with the computational force of a mobile processor of a currently common kind.

A further advantage of such a method according to the present invention is that obtaining of the electrical information on the basis of the heartbeat (beat-by-beat) is possible instead of for example based on continuous measurements during minutes or longer per session.

It is hereby especially advantageous that while applying the results of the method, such as in the below described preferred embodiments integrated the deal further explained, the predictability of the duration of a treatment of a disorder can be considerably improved. Because of this, the costs of such treatments can be considerably reduced and/or the capacity of a treatment room can be considerably increased. Also, the risks of such a treatment can be considerably lower at because the accuracy of the left or right ventricle and or the atria to be approached is considerably improved. Because of this, and necessary approaches of a ventricle are prevented. Thus, an unnecessary long duration of the procedure is prevented and the predictability of the duration improved, because of which the usage of time of the people and the degree of occupation, such as number of treatable patients per time unit of the treatment rooms is improved.

By lowering the fold risks with such treatments, the risk of infections is significantly reduced.

The level of skill of performing persons of such treatment may be subject to lower requirements. Also, the average number of persons in a treatment team can be reduced. According to a 1$^{st}$ preferred embodiment according to the present invention, the anatomical feature geography is a feature plane. According to a further preferred embodiment according to the present invention, the anatomical feature geography is an activation front.

Further preferably, the method comprises steps for constructing a further ECG feature vector based on shifting of the initial ECG feature plane to a position dividing the heart in a predetermined value, and repeating of these steps for constructing of a further ECG feature vector until a shift is smaller than a predetermined threshold or depending of an input in the user interface.

An important advantage of such a preferred embodiment is further specifying of the candidate area based on the initial vector. By applying these iteratively, this further specification may be improved until the difference between 2 successive iterations becomes so small that it can be assumed that the specification of the candidate area is determined sufficiently.

Further preferably, the predetermined value is 10-30%, preferably 15-20%, 20-25%, 10-15%, 25-30%, further preferably substantially 20%, further preferably of the muscle mass of the ventricles. Such values provide a practically effective example of a positioning of the beginning of the ECG feature vector.

According to a further preferred embodiment the method comprises steps for constructing of the weighted vectors based on electrode measuring information comprises steps for relating, such as multiplication with, of the electrode measuring information of the electrode sector with the predetermined ECG feature.

Further preferably, the predetermined anatomical feature geography is an ECG feature geography, such as a QRS wave, the P wave, the STT wave or the T wave. Such measuring data are instrumental with performing determinations relating to respective thereto attributed specific disorders.

According to a further preferred embodiment, the location information is obtained from an optical recording device, preferably an optical recording device for 3-D recordings, further preferably with two or more optical sensors. With such a device, location information can simply and reliably be obtained relating to a number of ECG sensors arranged relative to the torso.

The hearts model and or torso model is according to a further preferred embodiment obtained from a scanning device, such as an MRI, CT or sound echo device. Depending on available time and equipment the respective information can advantageously be obtained acutely, preparedly or based on historical measuring data for performing of this method.

In a case in which direct measurements on a subject for obtaining measuring data relating to the hearts torso model pose a problem, the heart model and or torso model of a subject is obtained from a data base with heart torso models, preferably in which steps are performed for choosing a heart torso model from the database with good correspondence with the subject. This enables that the determination of the candidate area can be performed without obtaining information relating to the hearts torso model by means of measurements on the body.

For the purpose of obtaining a determination of a candidate area in the bottom half of the heart, the origin is arranged in the proximity of the center of the bottom half of the heart. Such a determination and arrangement is advantageous as the QRS signals that can be obtained from an ECG device are the relatively strongest signals that are induced. Because of this, the reliability of these signals is relatively large and from that it follows that the determination of a disorder in the bottom half of the heart can be obtained with a relatively high reliability.

E.g. in case the heart disorder, such as PVC, is located at such a location that for example determination whether it is located in one ventricle or the other friend circle can be made with insufficient certainty, the methods according to a further preferred embodiment comprises applying in itself known further steps for analyzing of the course of the activation of the PVC. Following the determination of the candidate area, such application provides further information relating to the course of the activation for providing of a location determination of the initiation of the activation in the PVC.

Further preferably, the methods comprises steps for calculating a number, such as to, activation sequences, preferably one in the left ventricle and one in the right ventricle. Further preferably, the methods comprises steps for comparing the path of activation or the activation sequences with electrode measuring information of the ECG.

According to a further preferred embodiment, the method comprises steps for outputting image data relating to the hearts torso model, the initial ECG feature vector, and optionally the ECG feature plane and or the candidate area to a graphical user interface for rendering on a display screen. With this, a user, such as a doctor, can interpret a location determination or can input information relating to parameters for performing of the methods. Here too, the methods further preferably comprises steps for receiving of instructions of a user, such as for shifting the ECG feature plane and/or for inputting of a threshold value.

According to a further preferred embodiment, the method is applied for heart disorders such as ventricular tachycardia, atrial tachycardia, ischemic zones, Wolff-Parkinson-White syndrome, conductivity disorders or a combination thereof.

For the purpose of determining a further determination of the candidate area, ECG feature plane is shifted in the direction of the respective ECG feature vector. With this, the distance between the beginning of the vector and the candidate area is reduced such that the location thereof can be determined more accurately.

For constructing of weighted or normalized factors, the methods comprises steps for integrating per electrodes of the values of the ECG feature. By means of preferably addition of failures of all weighted or normalized figures, according to a further preferred embodiment, the initial ECG feature vector is determined.

A further aspect according to the present invention relates to a system for under application of a method according to one or more of the preceding claims determining of a candidate area of a heart disorder, comprising:

a processing unit, a memory coupled with the processing unit, receiving means for receiving location information relating to a number of ECG electrodes, receiving means for receiving electro data of the respective ECG electrodes, outputting means for outputting of result data and/or results comprising image data. Such a system provides advantages such as described in relation to the above described aspect of the method.

According to a further preferred embodiment, the system comprises a recording device, such as an optical recording device for determining of a position of respective ECG electrodes relative to a torso.

Further preferably, the system comprises a display screen and inputting means for inputting of instructions.

For the purpose of providing a user-friendly system, the processing unit, the memory and the recording device are integrated in one physical housing, comprising in memory program coding means for performing of the method according to the present invention and preferred embodiments as indicated in the above.

A further aspect according to the present invention relates to a method for controlling of operating of a medical device according to the present invention, preferably for the purpose of performing of a method according to the present invention.

A further aspect according to the present invention relates to a computer program product comprising computer program code that when executed on a processing unit configures the processing unit to execution of a method according to the present invention and preferred embodiments. As with preceding aspects advantages are provided such as described in relation to the above described aspect.

BRIEF DESCRIPTION OF THE DRAWINGS

Further advantages, features and details of the present invention will be described in the following in greater detail relating to one or preferred embodiments in the reference to the drawings. Similar yet not necessarily identical parts of different preferred embodiments may be indicated with the same reference numerals.

DESCRIPTION OF THE INVENTION

A preferred embodiment (FIG. 1) according to the present invention relates to a method for determining a candidate area of a heart condition, such as a PVC (premature ventricular contraction) causing part of the heart muscle, while applying information received from an ECG device and a processing unit. The method starts in step 1A with obtaining of a torso model in a way as described. Within this heart torso model, in step 1B an origin is determined for relating further calculations thereto. This origin is determined at either the center of the heart or the center of an area on which the determination is to be performed. Such a determination may be performed, in an in itself known way, for determination of a center of a mass. In step 2a, locations of ECG electrodes are obtained. Preferably, such locations are obtained from a 3-D camera. Tests have e.g. been performed with a so-called Kinect camera.

In step 2B, the position data of the electrodes on the torso are related to the heart torso model. Based on this, electrode measuring information can be processed while taking this into account. In step 3, from the ECG amplifier, electrode measuring information belonging to an initial ECG measuring is received by the computer.

In step 4, weighted or normalized factors between the origin and the ECG electrodes are constructed after which in step 5 the ECG feature vector is constructed relative to the origin.

In step 6, and iterative optimization by means of determining of the position of a further ECG feature vector based on a shift of the ECG feature plane to a new position is started.

In step 7, the feature vector is recalculated for this new position. Subsequently, in step 8 it is determined whether the vector position has been significantly modified relative to the initial vector that was determined in step 5. If this was not the case, the best vector position is determined, at least no further iteration is performed.

In step 10, based on a projection of the vector on the heart muscle around this projection, an area is selected, which area represents the candidate area.

According to a further preferred embodiment, subsequently in step 11, an activation sequence from a node within the PVC area is created and the sequence is optimized for obtaining of a subsequent activation estimate by means of analyzing the path of the activation of the PVC.

According to a further preferred embodiment, subsequently in step 11 and activation sequence from a note within the PVC area is created and this sequence optimized for obtaining a subsequent activation estimate by means of analyzing the path of the activation of the PVC.

Figure 2:
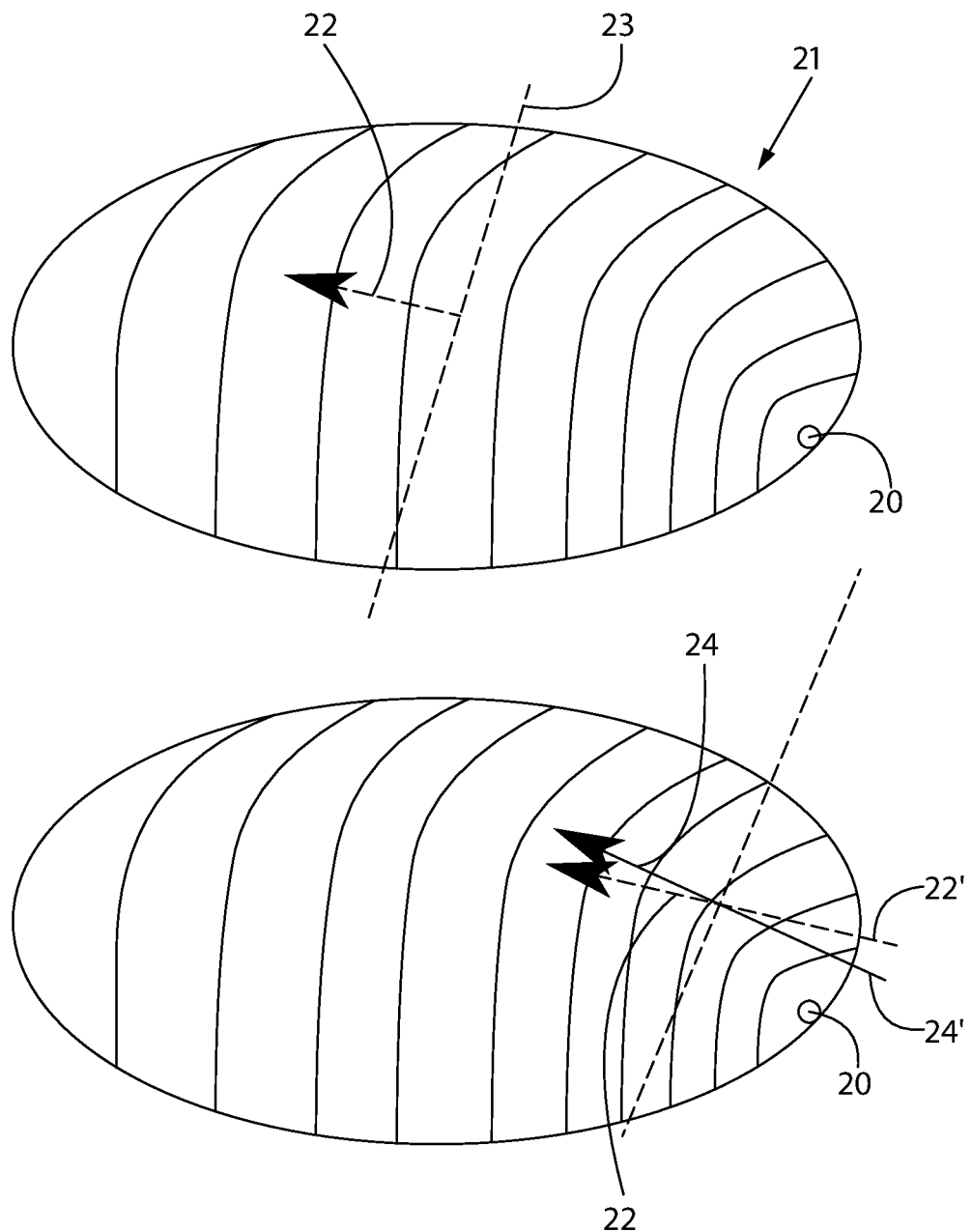
FIG. 2 is a schematic representation of a heart with an initial ECG feature vector, an initial ECG feature plane, and a shifting of the plane to a predetermined proportion of the heart tissue at both sides of the plane.

In FIG. 2, it is shown by means of 2 representations how in a schematically represented heart model 21 the initial vector 22 is arranged from the origin. Perpendicular to the initial vector, a separation plane 23 is arranged. The separation playing divides the myocardium substantially to equal parts when the origin is substantially positioned in the middle of the myocardium. After the determination of the initial vector 22, the plane is shifted in a way that substantially for instance 20% of the heart is located at one side instead of approximately 50%. The purpose thereof is to determine a further ECG feature vector 24 based on the herewith shifted origin such that the candidate area can be determined in such a way that with a high probability the PVC resides herein. The prolongation of the direction of the initial feature vector and the further ECG feature vector 24 provides an improvement in the 'pointing' to the PVC 20.

Figure 3:
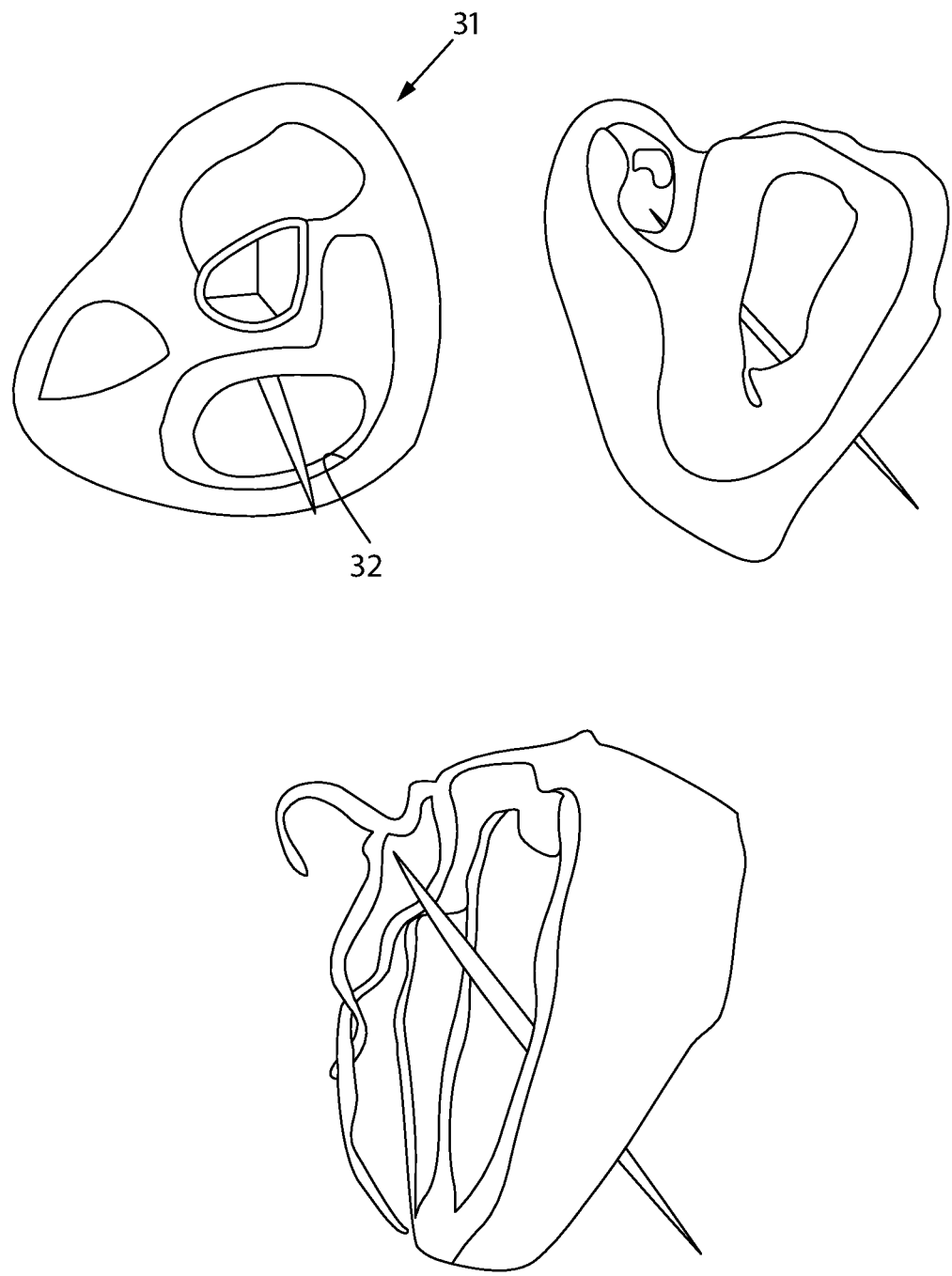
FIG. 3 is a schematic representation of a heart with an initial ECG feature vector based on a QRS wave.

FIG. 3 is a schematic representation thereof in a three-dimensional representation of the heart chamber. The difference is shown between an initial QRS axis and a further QRS axis. The initial QRS vector has a direction pointing away from an area 32 in which the PVC resides. The average QRS axis in FIG. 3 determines the plane according to FIG. 2 such that the plane is perpendicular to the arrow.

Figure 4:
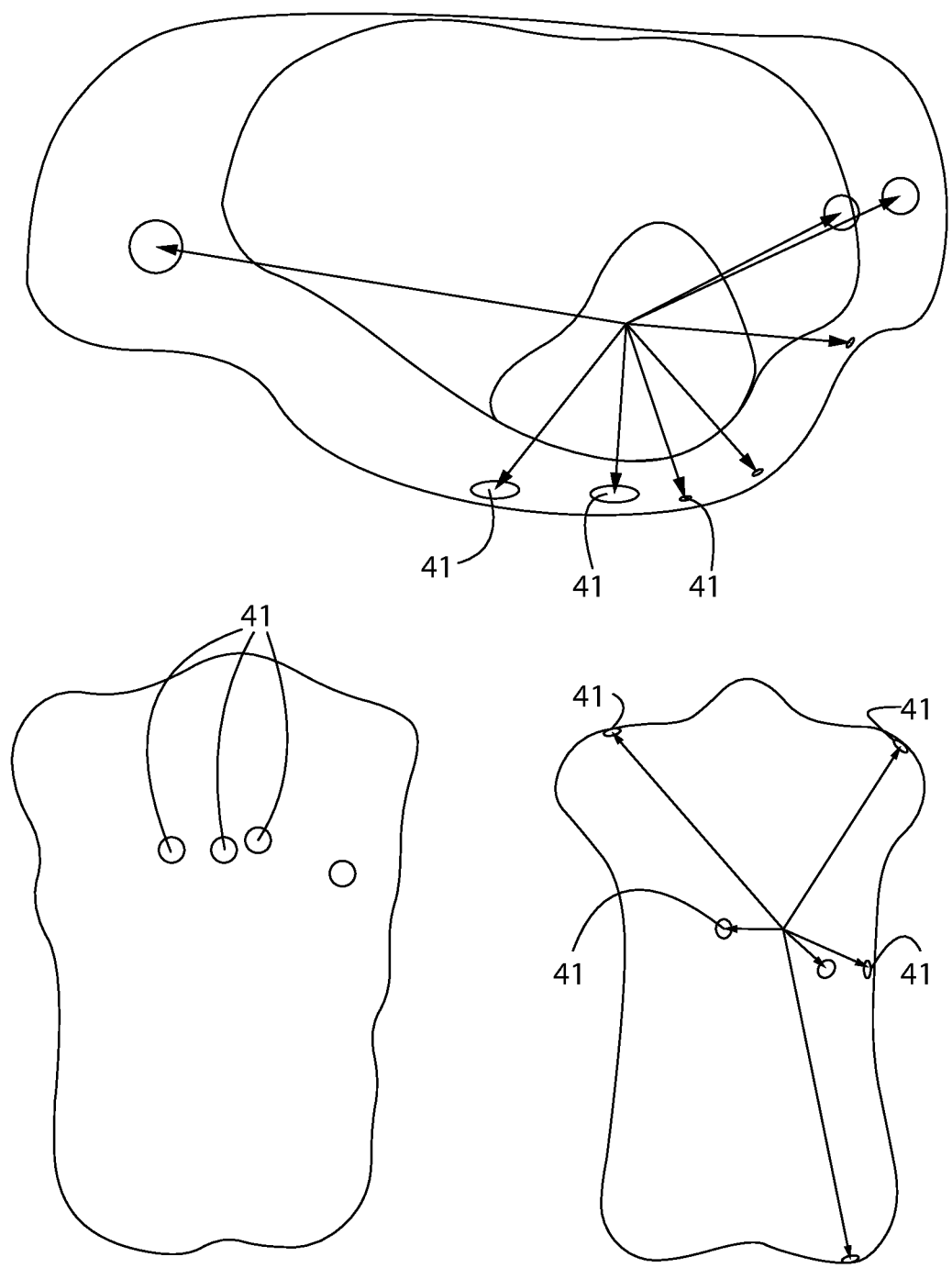
FIG. 4 is a schematic representation of ECG sensors on a torso.

In FIG. 4, it is schematically shown how ECG electrodes 41 may be arranged on a torso. From this it is perceivable on the basis of which, directions and distances the weighting or normalization needs to be performed. With larger distances to the heart model, the amplitudes are smaller and at different weighting is applied.

Figure 5:
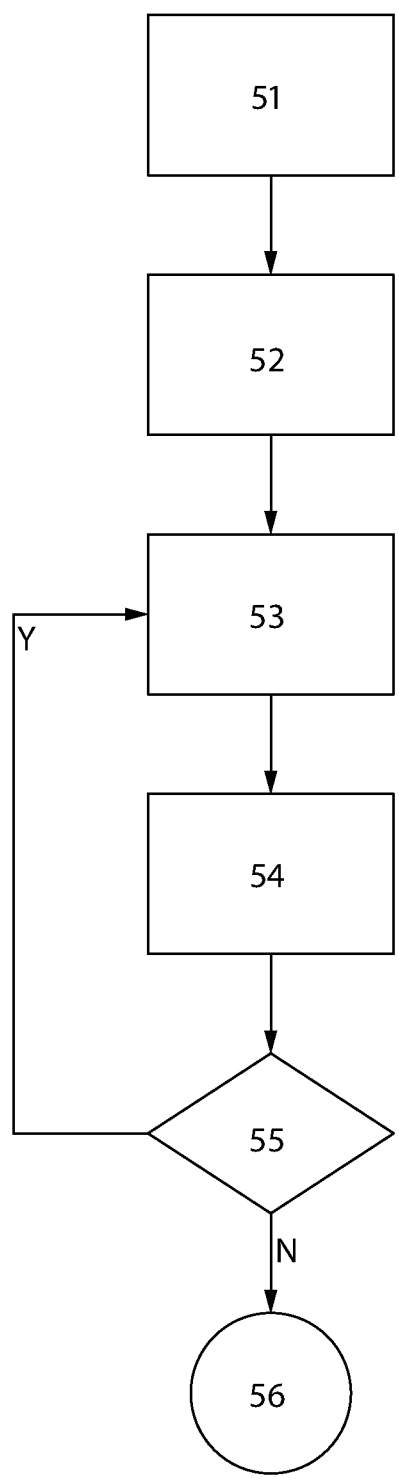
FIG. 5 is a schematic further elaboration of iteration steps for determining of the initial and further ECG feature vectors.

In FIG. 5, a preferred embodiment of the method is close a specified shown based on the example of the QRS wave. In step 10 FIG. 5, the center of mass of the ventricle is determined, in other words the origin. Use is being made of in itself known ways of calculation for determining the center of a mass. The result is the $LV_{CM}$. based on the $LV_{CM}$. the initial factor direction per electrode is calculated. In step 3 of FIG. 5, the QRS vector is shifted in the direction of the QRS origin until 80% of the tissue is located on the side directed away from the PVC of the plane. In step 4, the vector is recalculated with the new position according to steps as shown in FIG. 5. In case it is determined in step 55 of FIG. 6 that the position was changed in such a minimal way that the distinct criteria has been fulfilled, the method is ended, otherwise the method proceeds in step 3.

Figure 6:
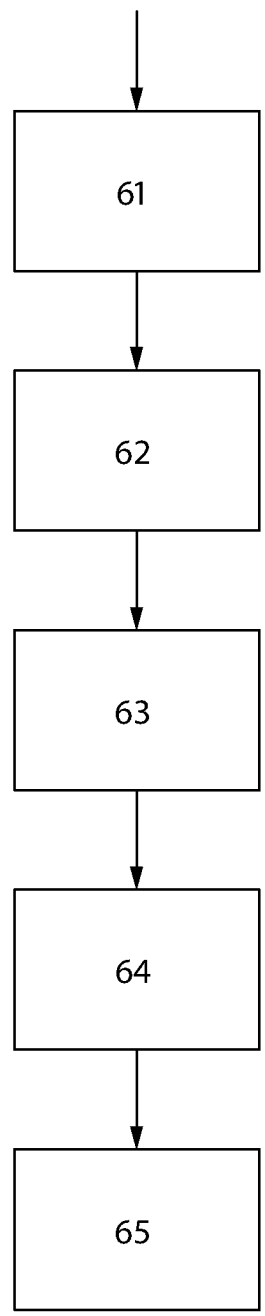
FIG. 6 is a schematic further elaboration of determining of a QRS vector as feature vector.

In FIG. 6, a method is shown for determining of an aggregated QRS vector. To determine the average QRS, the integral per electrode is determined. This is used in for example FIGS. 2 and 3. In step 61, per electrode of the ECG, a vector is determined, in which it is defined that the vector r lead=electrode position minus origin. This is a factor determining the distance and direction of the electrode to the origin. In step 62, the, in case of 9 electrodes, 9 factors are normalized. In step 63, the QRS vector is calculated by means of an integral per electrode factor $R_{QRS}$=vector r×integraal QRS. In step 64, the QRS vector per electrode are summed which results in the QRS vector 65.

Figure 7:
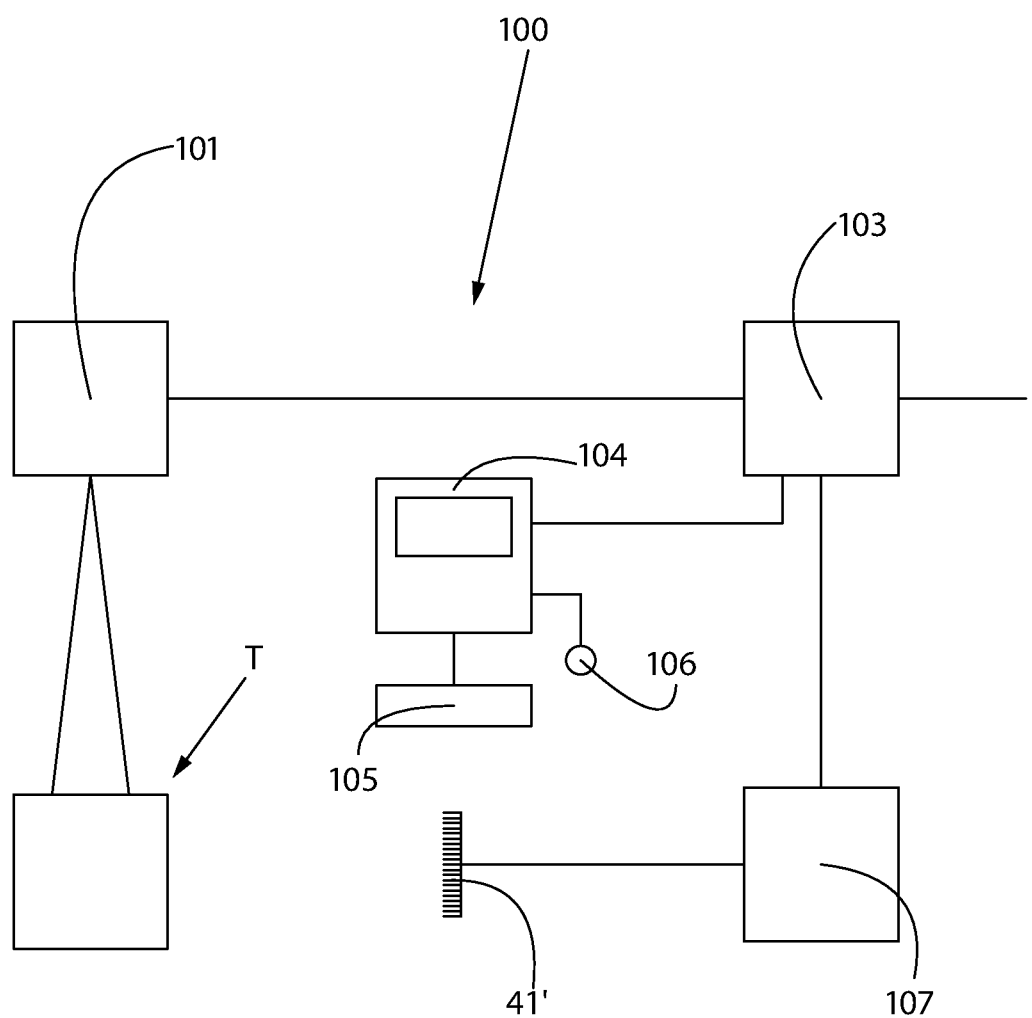
FIG. 7 is a block diagram of a preferred embodiment of a system according to the present invention.

In FIG. 7, a preferred embodiment is shown of a system for performing the method. A three-dimensional camera 101, for detecting ECG electrodes arranged at a torso, is arranged above a torso the (schematically shown) of a person. The camera is suitable for moving thereof relative to the torso such that from several sides the torso can be recorded for detecting of the ECG electrodes in place. Data from the camera are transferred to a computer 103. The computer 103 is connected to a monitor 104, keyboard 105 and mouse 106 for receiving input data from these peripherals from a user and for outputting of image data to the user. The computer is furthermore coupled with an ECG amplifier 107 that in its turn is coupled to ECG electrodes on the torso T. A practical number of electrodes that is supplied is between 4 and 16, preferably substantially 9. A larger number for achieving a higher resolution is envisaged and dependent on the surroundings in which the installation is applied also usable. The skilled person would be able to determine the number of electrodes as a correct choice based on available equipment.

An example of an implementation in the form of an algorithm according to a preferred embodiment relating to vectors is the following:

calculate for each vertex of the heart model:
a) an initial factor positioned on that vertex, and
b) an average QRS vector localized half way the line between the measured vertex position and the vertex on the heart geometry most remote taking into account the anisotropic nature of the propagation in the myocardial tissue.

Calculation of an initial anatomical axes comprises steps for:

determining all nearby vertices within 20-45 mm. A nearby axes is a nearby axes when a line through or over the myocardium can be drawn, determining of the average factor between the proposed PVC location and the nearby vertices, if the length of the resulting vector is less than a predetermined minimum (for example smaller than 2 mm) the proposed position does not generate a clear initial vector.

Figure 1:
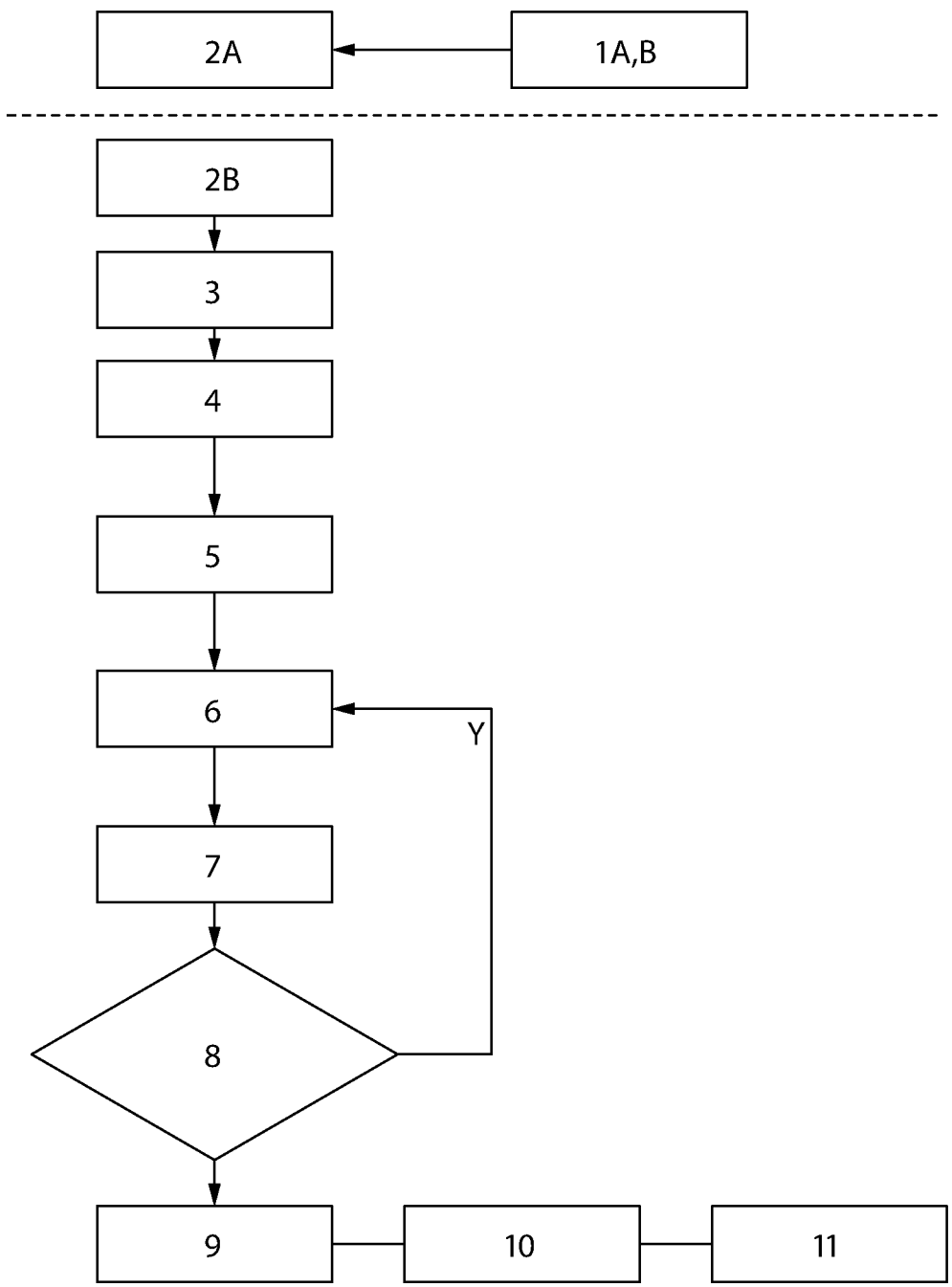
FIG. 1 is a flowchart of a 1$^{st}$ preferred embodiment according to the present invention.

A method according to the below algorithm is an alternative for the method according to the preferred embodiment according to FIG. 1.

```
For each vertex of the heart model:
    Initial vector: use the first 20 ms after onset QRS of the ECG
    initialECGVector(i) = compECGVector(vertex i, ECG(onsetQRS -> onsetQRS + 20ms)
    determine most distant vertex
    faraway Vertex = mean(all vertices more than 90% of the maximum anisotropicDistance for vertex i )
    // for anisotropic distance see reference above
    QRS-vector: use the first 20 ms after onset of
QRS of the ECG QRS vector:
    QRSECGVector(i) = compECGVector(vertex i + 0.5 x (farawayVertex – vertex i) , ECG(QRS duration)
    initial anatomical QRS-vector
    vertexAreas = for each vertex ⅓ of the area connected triangles per vertex
    meanInitialAnatomicalVector(i) = [0 0 0]
    n=0;
    for each vertex(j)
        if length(vertex(i) – vertex(j)) < 25 mm
            meanInitialAnatomicalVector(i) = meanInitialAnatomicalVector(i) + length(vertex(i) – vertex(j)) x vertexAreas(j)
        end
    end
    meanInitialAnatomicalVector(i) = meanInitialAnatomicalVector(i) / n;
    Anatomical QRS-vector
    AnatomicalAxis(i) = (farawayVertex – vertex i)
end
```

-continued

```
    origin of the activation location
    anglesECG_AnatomicalVector = acos(normalize( QRSECGVector ) · normalize( Anato-
micalAxis )
    acos is inverse cosinus
    anglesInitial_ECG_AnatomicalVector = acos(normalize(initialECGVector) · normal-
ize(meanInitialAnatomicalVector )
    estimated_activationStartArea = (1 − normalize(anglesECG_AnatomicalVector)) x
                        (1 − normal-
ize(anglesInitial_ECG_AnatomicalVector))
    For each vertex i
        If estimated_activationStartArea(i) > 0.9
            Compute the correlation between measured ECG and the simulated ECG for
activation starting from vertex i
        end
    end
```

The PVC is determined by the angle

The node with the highest correlation is the node from which the activation starts and the position of the initial and the average QRS factor follows.

Relating to this, it is of importance that the calculations are performed on the basis of all vertices (i). For the vertex i were by the average difference between the anatomical factor and the ECG factor is smallest, it is determined that this ECG vector is the best match with the anatomical factor and thus best the PVC indicates.

Figure 8:
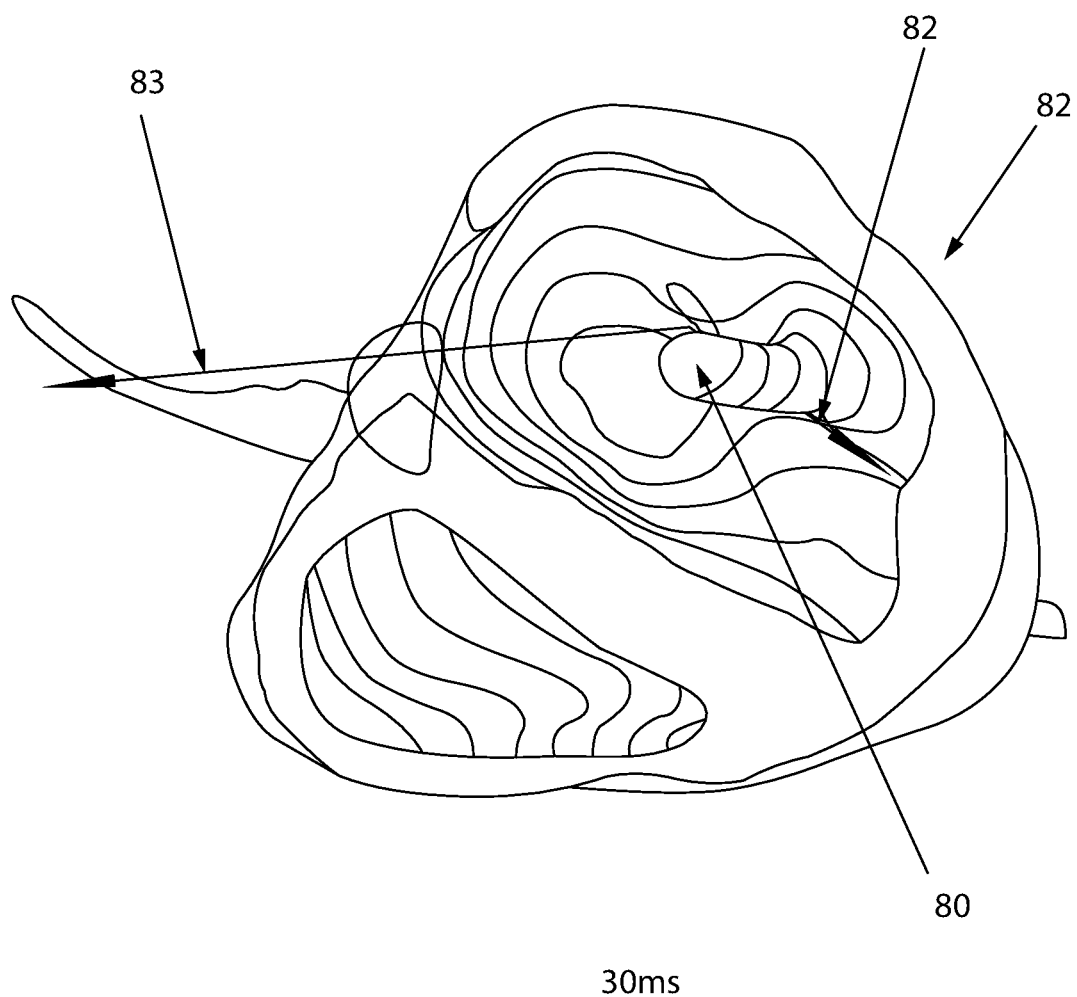
FIG. 8-10 are schematic representations of a heart with vectors according to the present invention.
Figure 9:
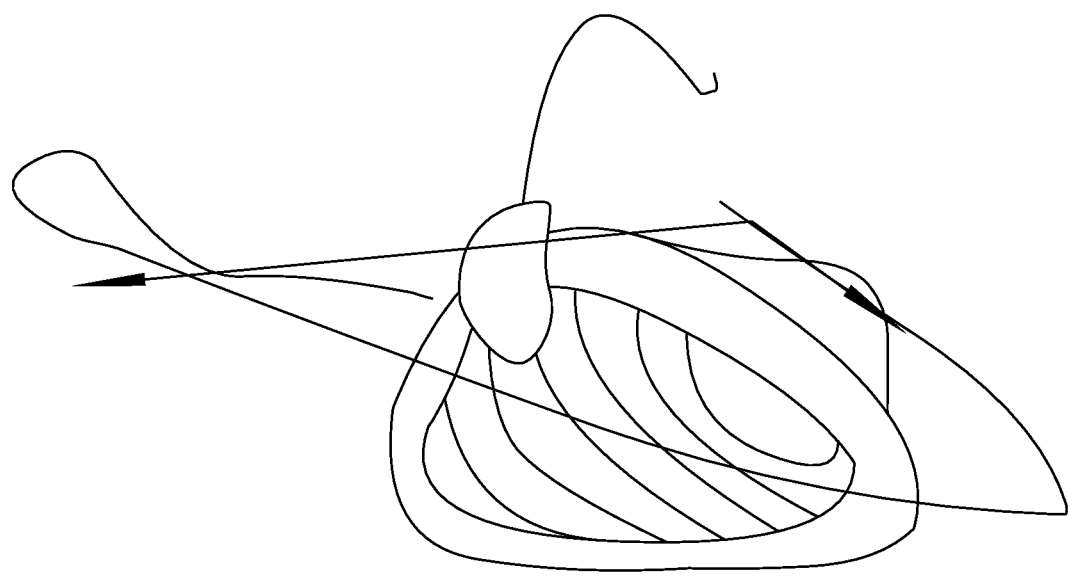
Figure 10:
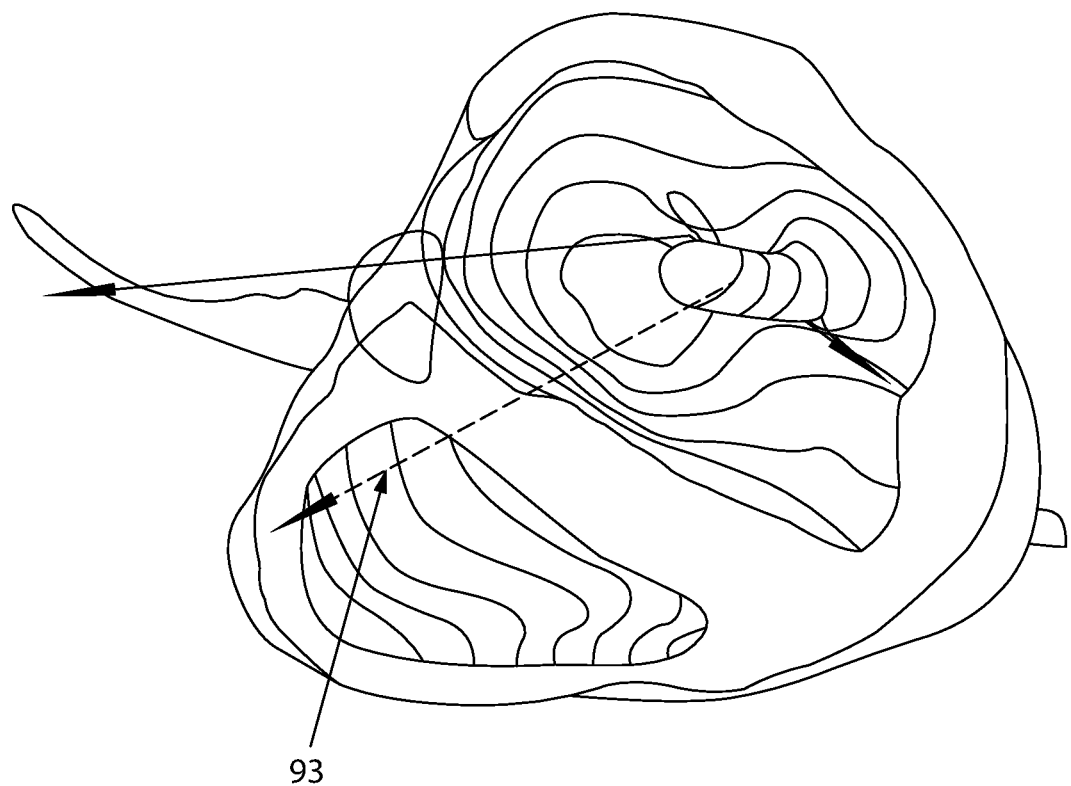
Figure 11:
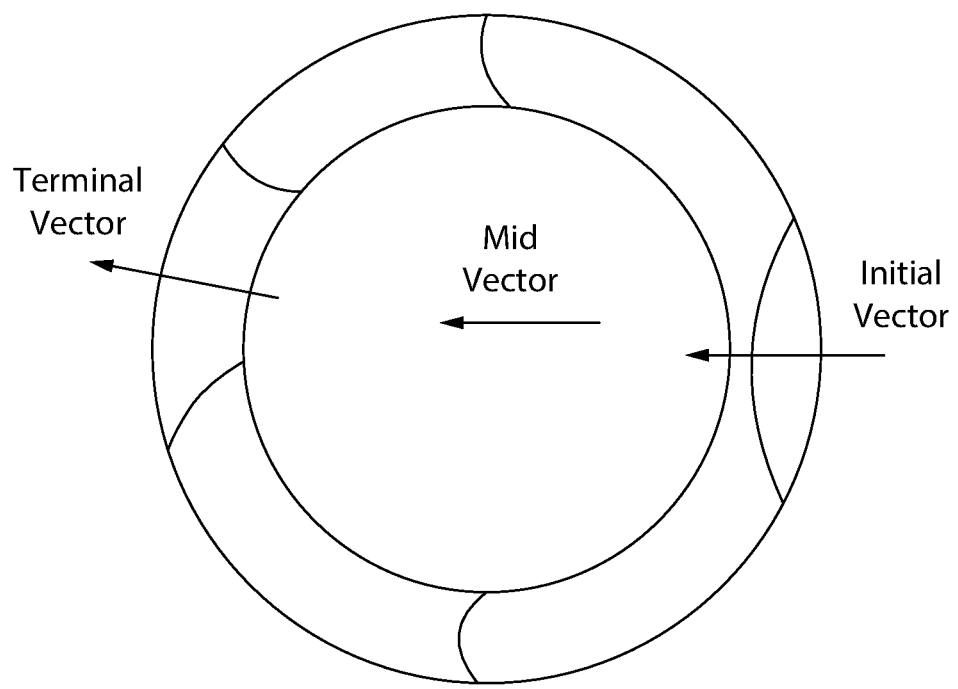
FIG. 11 is a schematic representation of progress vectors according to the FIGS. 8-10 in a schematic representation of an anatomy.

The FIGS. 8-10 are examples taken on, from the initiation of the heart cycle 30 ms, 19 ms and 40 ms. compHeartAxis: Computation of the anatomical heart axis vector applying a formed 3-D model, the anatomical access is calculated based on electrode locations in the anatomical heart model. The anatomical axes is calculated by means of:

1) determining a plane through the vertices building the mitral annulus, 2) project all endocardial points on this valve plane, 3) accounts for hearts that are more spherical, which have caused the bulging of the anterior, posterior and free wall. Consequently, the center of the projected endocardial points moves towards the lateral wall.

4) the axis of the heart is calculated as the 3D vector between the mid-basal heart axis position and the most distant endocardial vertex relative this basal point.

For each patient the heart axis was computed, resulting in an angle between the X, Y, and Z-axis. The X-axis is defined as the posterior to anterior line, the Y axis as the right lateral to left lateral line and the Z axis as the line from feet to head.

compECGVector(vecPos,ECG): Computation of the ECG vector for a given position (vecPos) and the given ECG Obtain the 3D positions on the ECG electrodes (ECG_electrode_pos)

For the given vector position (vecPos) compute the vectors from vecPos to ECG_electrode_pos and normalize (ECG_electrode_pos−vecPos)

Sum the signals of the ECG over time (ECG_integral)

ECGvector=sum (ECG_integral×normalize (ECG_electrode_pos−vecPos))

compECGVectorLoop(vecPos,ECG): Computation of the ECG vector for a given position (vecPos) and the given ECG Obtain the 3D positions on the ECG electrodes (ECG_electrode_pos)

For the given vector position (vecPos) compute the vectors from vecPos to ECG_electrode_pos and normalize (ECG_electrode_pos−vecPos)

ECGvectorloop(t)=sum (ECG(t)×normalize (ECG_electrode_pos−vecPos)).

Figure 12:
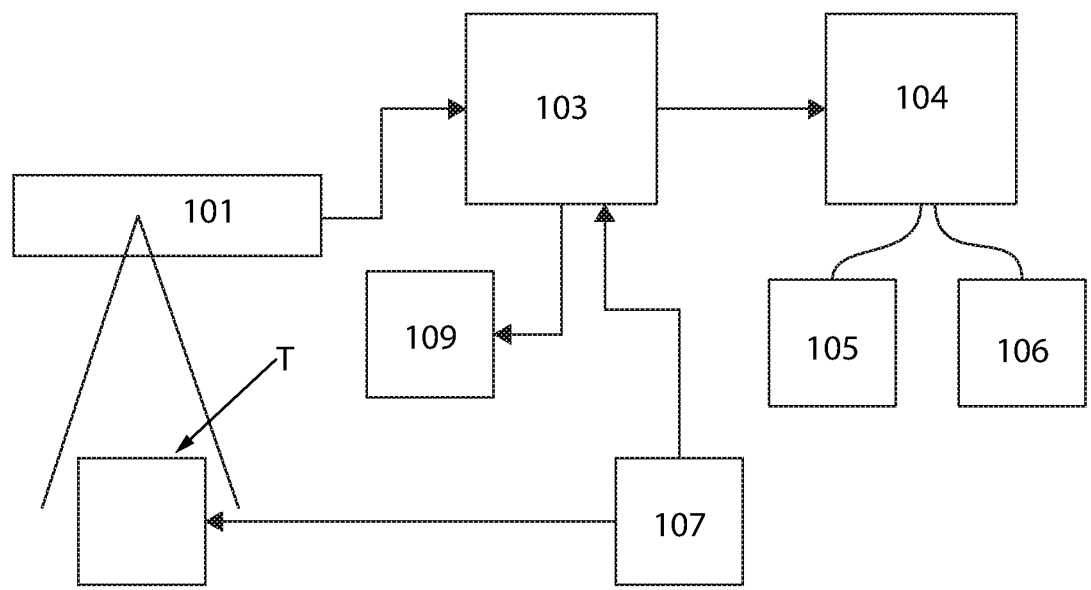
FIG. 12 is a schematic overrepresentation of a system according to a further preferred embodiments.
Figure 13:
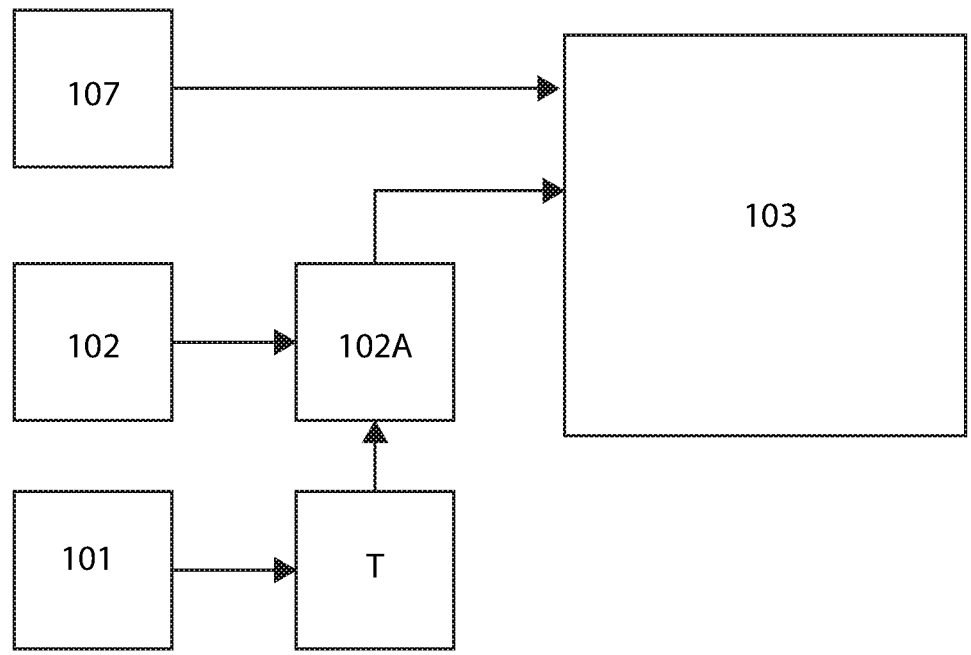
FIG. 13 is a schematic representation of a system according to a further preferred embodiments.
Figure 14:
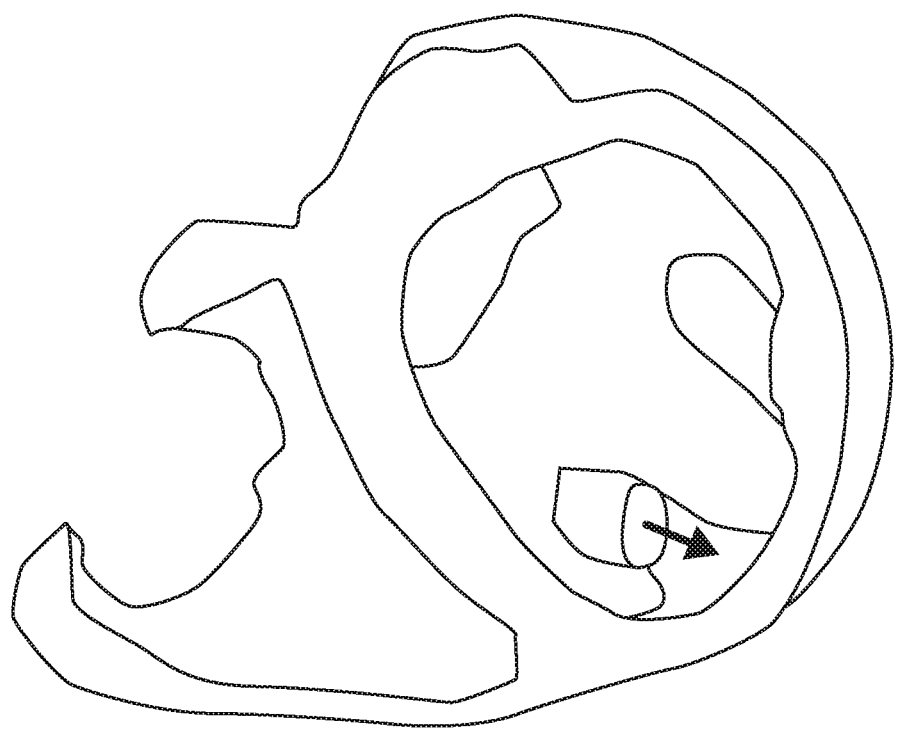
FIG. 14 is a schematic representation of a with Darrin a schematically represented anatomical vector

FIG. 12 shows a system 121 similar to the system according to FIG. 7 however comprising a row was 109 for automatically controlling link of the catheter with the tip from the catheter to the area to be treated. A robot for doing this is known in itself for guiding all of the catheter by means of a wire towards the heart. The present invention and the present preferred embodiments are directed at towards the device performs a method on the basis of location determination on the basis of the ECG related to the model. In this way, the in itself known controlling instructions to the robot are assembled in order to control the robot based on the location determination according to the present invention by the computer 103.

The purpose is to guide the robot to the area. A further purpose is that it is prevented that expensive catheters are required. It is possible in itself to have the robot perform the procedure fully automatically but it is the preferred method to bring the catheter in the heart chamber manually after which the ablation and the location determination of the ablation is performed by the computer and the robots. To this end, the catheter can move freely within the walls of the heart. Based on the location determination, the catheter is thus brought in the correct chamber of the heart manually before the ablation.

For determining the position of a catheter in a heart, according to the prior art costly detection devices are required in combination with costly catheters. The reason for this is that the detection for the location determination is performed based on two technologies, location determination based on an electrical field with an electrical field measuring device in the catheter and a location determination based on magnetic fields with a recorder for the magnetic field in the catheter. Such equipment is costly and requires setup and maintenance in a reliable, certified manner.

In order to prevent such a disadvantage, the present invention provides a location determination based on the ECG, which location determination is accurate because of relating all of the measured data of the ECG to the model by the matching of the electrodes of the ECG to the model.

The robot is controlled based on an initial location determination of the tip of the catheter by having the catheter exert a stimulus pulse when it hits the wall. Whether the tip is located against the wall is determined by an electrogram of the tip that is represented on the display screen of the ECG. Alternatively, it is determined that the wall is touched by means of a pressure sensor. As soon as the tip touches the wall, the tip can activate the heart muscle by means of a stimulus after which the location of the activation is determined in the same manner as the location of the PVC in the above.

Based on the earlier performs location determination of the PVC in the model, and with that in the heart, subsequently a control signal is generated for moving the tip of the catheter towards the location of the PVC. To this end, it is envisaged that a number of iterations of this process are performed. After performing all of the movement towards the PVC, the new location of the tip of the catheter is determined on the basis of a measurement of a stimulus pulse exerted by the tip.

The present embodiment provides thus both the application of a cost-effective catheter with tip and a reliable positioning of the tip for the purpose of ablation of the PVC area.

Localization (FIGS. 13-17) of the site of origin of a premature ventricular contraction (PVC) according to the present invention prior to ablation facilitates the planning and execution of the electrophysiological procedure. In clinical practice the targeted ablation site is estimated from the standard twelve lead ECG. The accuracy of this ECG based estimate in itself has limitations, particularly the localization of PVCs originating from the papillary muscles frequently fails. Electrocardiographic imaging (ECGI) techniques are devised by the inventor to support the localization of such PVC, by taking the cardiac anatomy into account. The present invention provides to accurately detect the location of PVC specifically on the papillary muscle using only a 12-lead ECG.

Components (FIG. 13) used in this embodiment comprise: 1) endocardial and epicardial cardiac anatomy and torso geometry 102 are derived from MRI and formed into a model of meshed nodes, 2) the actual electrode positions are derived from a 3D image and linked to the model and 3) the 12 lead ECG measurements 102a are related to the model with leads positions. The embodiment localizes the PVC origin by matching the anatomical isochrone vector with the ECG vector. The predicted PVC origin is compared to the site of successful ablation or stimulation.

Tests. Three patients have undergone electrophysiological mapping and ablation of PVCs at the papillary muscles and were studied. The embodiment localized the PVC origin for all patients to the correct papillary muscle, specifically to the base, mid or apical walls. Results included that this novel vector-based ECGI method according to the embodiment with the standard 12-lead ECG shows promise to localize the origin of PVC accurately to specific sites on the papillary muscles.

Catheter ablation is an effective therapy for treatment of symptomatic premature ventricular contractions (PVC). Prior to the ablation procedure, the targeted anatomic ablation site is estimated using qualitative descriptions of the standard 12 lead ECG waveforms. With these qualitative descriptions sometimes have shown limitations in localizing the PVC origin to the cardiac anatomy In particular the localization of the arrhythmic origin in the papillary muscles fails. Electrocardiographic imaging (ECGI), using a patient specific model of the heart according to embodiments are envisaged to enhance the accuracy of the PVC origin localization.

The embodiment has been capable to localize the PVC origin to any part of the myocardial anatomy including from a papillary muscle based on the standard 12 Leads ECG being used to localize the origin of ventricular activation originating from either the inferior or lateral papillary muscle.

Three subjects who underwent radiofrequency (RF) ablation of symptomatic idiopathic PVCs were included in the test. Each patient signed an informed consent, two female (57 and 80 years) and 1 male (32 years).

A patient specific cardiac and torso model derived from MRI and patient specific electrode positions derived from a 3D Kinect camera were used to provide the model. For all 3 patients, the morphing software according to the embodiment was used to reconstruct MRI based anatomical models of heart, lungs, and thorax (7). For all three ventricular patient specific models the posterior and anterior papillary muscles were incorporated in the model.

The electrode positions in the model need to be determined accurately to reduce localization errors of the PVC origin. Tests were performed based on a commercially available Kinect camera and software created by the inventors used to image the electrode positions on the chest wall. Imaging was performed at the end of the preparation of the patients just before starting the ablation. The 3D images were subsequently matched to the patient specific model of the patient. The matched image allowed accurate positioning of the electrode positions on the thorax model.

Standard 12-lead ECGs sampled at 977 Hz were recorded during the ablation procedure using Cardiolab, GE. The visualized, filtered, clipped, data was stored. The clinical ECGs containing a PVC and/or a well described pacing location the 12 lead ECG was exported to an external device over a universal serial bus and fed into a Cardiac Isochrone Positioning System. A representative PVC of the clinical ECG waveforms was selected for each patient. Fiducial points, i.e. onset and end QRS, were determined manually. Subsequently the ECG was baseline corrected between two successive QRS onsets. No additional filtering was applied to any of the ECG signals. As lead I, II, and III are using the $V_R$, $V_L$, and $V_F$ and thus allows more weight on the extremity leads. The nine signals $V_R$, $V_L$, $V_F$, $V_1$-$V_6$ referenced to the Wilson central terminal were used.

The PVC was located by the device according to the embodiment. According to the embodiment, a myocardial distance function was used to test cardiac activation waves. For the ventricle, a myocardial distance function was used to simulate the heterogeneous nature of the ventricular activation as well as a fastest route algorithm.

Using this embodiment, the simulated activation originating from a ventricular position that created the best match between simulated and measured ECG was selected as the PVC origin. According to the embodiment, the ECG derived vector direction was compared to the anatomical vector direction. The ECG derived vector $(\overrightarrow{V_{ecg}(t)})$ at time t of the QRS is determined by $$\overrightarrow{V_{ecg}(t)} = \sum_{lead=1}^{9} \frac{(\overrightarrow{x_{lead}} - \overrightarrow{v_{pos}})}{|\overrightarrow{x_{lead}} - \overrightarrow{v_{pos}}|} ecg_{lead}(t),$$

where $x_{lead}$ is the electrode position on the chest wall of lead (VR, VL, VF, or V1-6), and $v_{pos}$ the chosen vector position in the heart.

Figure 15:
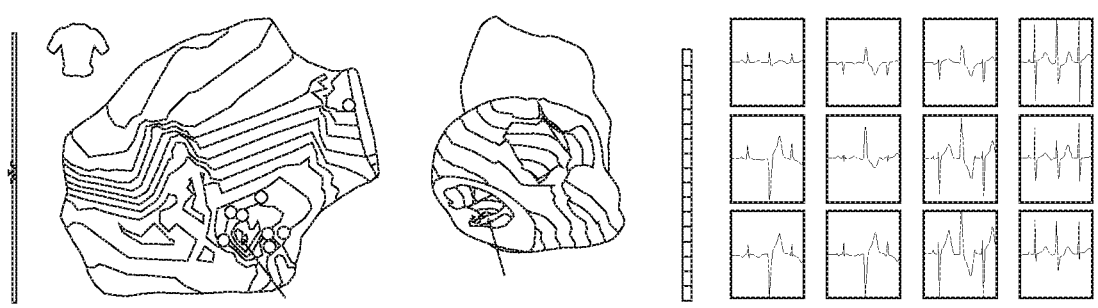
FIGS. 15-17 are graphical representations of measurements and model representations of three described subjects.

The anatomical vector (FIG. 14) is derived from the simulated isochrones, FIG. 15 showing activation wave front originating from the tip of the papillary muscle S(t) after approximately 10 ms, including the single anatomical based vector representation $\overrightarrow{V_{anatomy}}$.

An isochrone represents a surface within the myocardium at the moment of depolarization. This 3D surface S has a direction, for which a mean single anatomy derived vector can be computed:

$$\overrightarrow{V_{anatomy}(t)} = \int_{S(t)} \vec{s}_n dS,$$

in which $\vec{s}_n$ is the normal of dS in the direction of the activation surface S. As this is directed at the directions, the angle α(t) between both vectors at time t is computed by:

$$\alpha(t) = \cos^{-1}\left(\frac{\overrightarrow{V_{anatomy}(t)} \cdot \overrightarrow{V_{ecg}(t)}}{|\overrightarrow{V_{anatomy}(t)}||\overrightarrow{V_{ecg}(t)}|}\right)$$

For the localization of the PVC origin 3 angles have been computed:
1) the initial (t=30 ms),
2) the mid-QRS vector (t=0.5×QRS duration), and
3) the terminal QRS vector (t=0.8×QRS duration).

The initial vector potentially localizing the PVC origin most accurately, the angles were weighed:

$$\alpha_{tot} = \alpha_{initial} \times (\alpha_{midQRS} + \alpha_{terminalQRS})$$

The vertex with minimal $\alpha_{tot}$ localizes the PVC origin. The weighing can be described as:
a) the mid and terminal QRS angles determining the area of the PVC area globally and
b) the initial vector localizing the PVC origin within this area.

The patients that underwent electrophysiological procedure and ablation of symptomatic PVCs originating from the papillary muscles were studied (TABLE 1). Both the electro-anatomical maps (NAVX, CARTO) and the clinical EP report were used for the 12 lead localization. Patient 1 was identified with non-ischemic cardiomyopathy, the other two patients had no cardiac history. Scar was not detected in any of the patients. The electro-anatomical mapping systems do not have the capability to map the papillary, as shown in FIGS. 2-4. Therefore the EP procedure report is used to confirm these cases indeed are papillary muscle ablation cases. The exact location on the papillary muscle, tip versus base for instance, were not accurately determined. In each of the CIPS results figures the vector trajectory, from localized origin till end of the activation wave, is shown as a colored line. The line colors are the same as used in drawing the isochrones (every 10 ms) on the ventricular myocardium. Patient 1 showed A PVC originating from the basal part of the posteromedial papillary muscle (FIG. 15). The embodiment localized the PVC close to the posterior part of the papillary muscle, visualized as the start of embodiments' vector trajectory originating from this area (top left vertical line) as follows.

Figure 16:
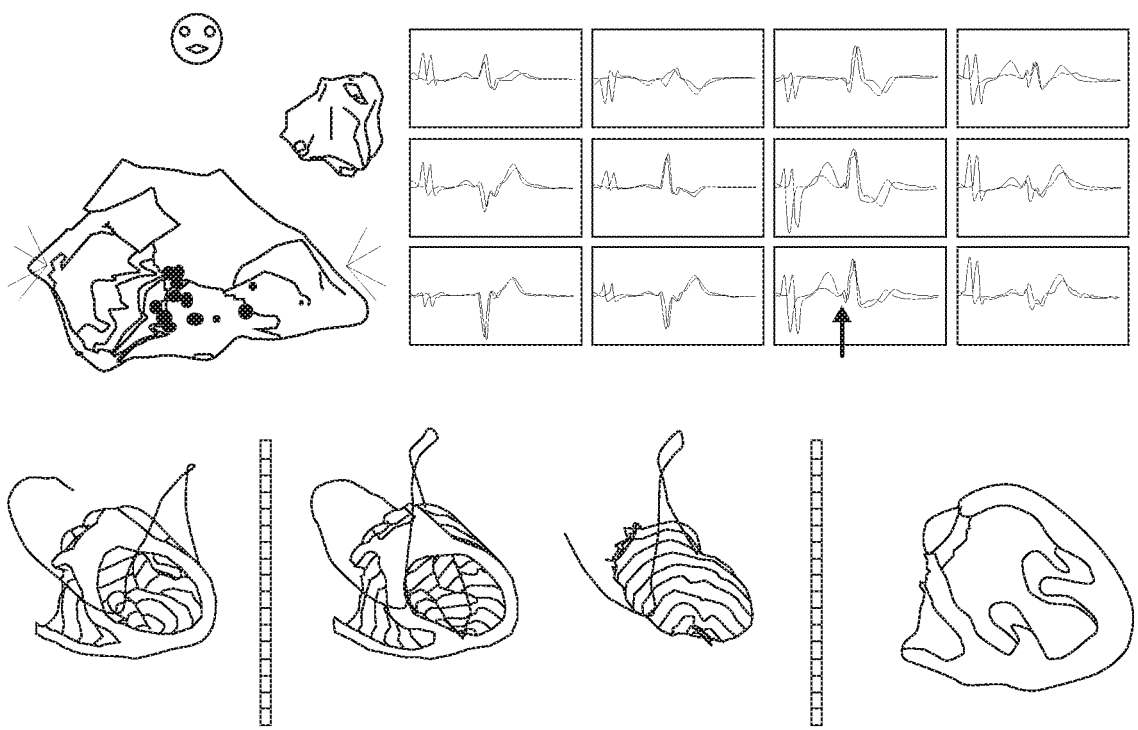

FIG. 15 Results for patient 1. Left panel: The NAVX electro-anatomical map of the PVC. Middle panel: The isochrones and derived PVC origin as localized by the embodiment. Isochrones are represented at every 10 ms. The colored line is the embodiment vector trajectory, starting in the posteromedial papillary muscle, moving towards the apex (top left vertical line) subsequently showing dominantly activation going in the superior anterior direction ending in the right RVOT region. Right panel: the 12 lead ECG as used by the embodiment. All embodiment results are shown in AP view. FIG. 16 shows Results for patient 2. Top-Left panel: The CARTO electro-anatomical map of the PVC. Top-right panel: the 12 lead ECG of PVC 1 and 2 as used by the embodiment. Bottom left panels: The isochrones and derived origin of 2 PVCs as localized by the embodiment. Isochrones are drawn every 10 ms. The colored line is the CIPS vector trajectory, starting at the tip of the anterior papillary muscle (PVC1) or the base of the same papillary muscle (PVC2), and subsequently showing dominantly activation going in the superior posterior direction ending at the base of the RVOT for the first PVC, and left lateral for the second PVC. Bottom right panel: AP view of a cross-section of the ventricles. Both papillary muscles are in the same plane. Anterior or posterior papillary muscle classification does apply to both papillary muscles as both papillary muscles are in the same AP plane. All results of the embodiment are shown in AP view.

Patient 2 showed 2 different PVC morphologies in the 12 lead ECG (FIG. 16). Differences in QRS morphologies can be majorly be found in the precordial lead V1, V5 and V6. PVC 1 was localized by the embodiment to the tip of the anterior papillary muscle as also shown by the Carto electro-anatomical map. PVC 2 was localized to the base of the same papillary muscle. The deeper Q-wave in V1 of PVC 1 compared to PVC 2 might supports the distinction between tip and base of the papillary muscle by the embodiment.

Figure 17:
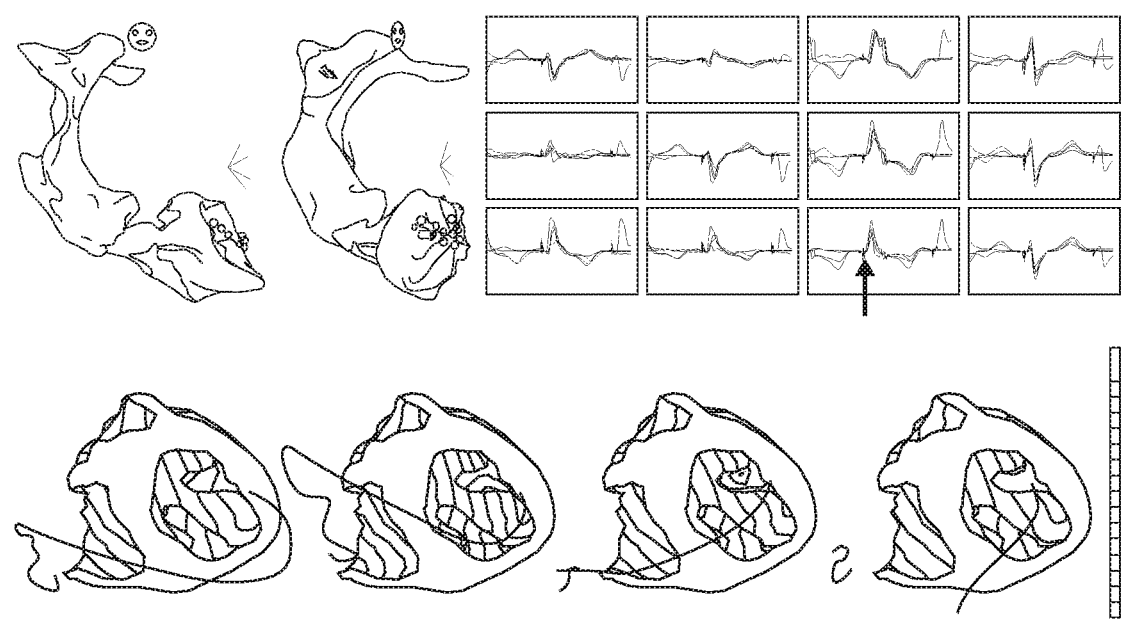

FIG. 17 shows Results for patient 3. Top-Left panel: The CARTO electro-anatomical map of the PVC. Top-right panel: the 12 lead ECG of PVC 1 and 2 as well as 2 pace maps (PM), one at the tip of the papillary muscle and one from the mid papillary muscle. Isochrones are drawn every 10 ms. Bottom left panels: The isochrones and derived origin of 2 PVCs and 2 PM as localized by the embodiment. The colored line is the vector trajectory according to the embodiment, starting at the tip of the anterior papillary muscle (PM1) or the mid papillary muscle. For PVC2 this is inferior mid, PM1 superior mid, and for PM2 posterior mid. All results are shown in AP view.

Patient 3 showed 2 different PVC morphologies, and two different pace maps were recorded, one from the time of the papillary muscle and one from the mid position of the PAP (FIG. 17). For patient 3 the position of the ablation lesions were confirmed with a separate intra-cavitary echo image (ICE).

In these tests it is shown that the embodiment is able to localize PVCs to different parts of both papillary muscles. The new anatomical based vector based approach is able to localize the initial vector generated by a PVC to the correct papillary muscles using just the standard 12 lead ECG.

The vector based algorithms according to the embodiment relies on two components: the anatomical vector, derived from the cardiac anatomy and the assumption of a homogeneous propagation activation wave using the fastest rout algorithm, and on the computation of the initial vector of the 12 lead ECG. Especially the latter can be undetectable by noise. The papillary muscle cases show this clearly, as the amplitude of the initial QRS is often less than 0 .1 mV, see the ECGs in FIGS. 15-17.

This needs to be taken in into consideration recording the ECG, because previous attempts to localize PVCs required the complete QRS waveform. The localization of the PVC origin in current embodiments of the vector based algorithm is substantially determined by the comparison of the initial ECG and anatomical vector direction. For the initial part of the activation and consequently the ECG this single vector provides a preferred representation of the ventricular activation.

TABLE 1

Patient characteristics, gender, age, weight, chest circumference and ejection fraction (EF). None of the patients had a history of myocardial infarction. During the ablation procedure no scar tissue was found.

| Patient | Gender | Age | Weight kg | Chest circumference | F |
|---------|--------|-----|-----------|---------------------|---|
| 1 | F | 57 | 60 | 902 | 0 |
| 2 | M | 32 | 96 | 1049 | 8 |
| 3 | M | 28 | 64 | 887 | 0 |

TABLE 2

Comparison between the localization of ablation site from the electro-anatomical maps and the origin of the PVCs based on CIPS on the papillary muscles (PAP).

| Patient | Location ablation site | | embodiment localization | |
|---------|------------------------|-----|-------------------------|---|
| * | posteriomedial PAP | VC1 | I | posteriomedial PAP mid |
| | anterior PAP (base) | VC1 | I | anterior PAP (tip) |
| | anterior PAP (base) | VC2 | I | anterior PAP (base) |
| | anterior PAP | VC1 | I | anterior PAP (tip) |
| | anterior PAP | VC2 | I | anterior PAP (mid) |
| | anterior PAP tip | M1 | I | anterior PAP (mid posterior) |
| | anterior PAP mid | M2 | I | anterior PAP (mid anterior) |

* The term anterior papillary muscle is used although it would be more correct to use the term posterior papillary muscle.

The present invention has been described in the foregoing on the basis of several preferred embodiments. Different aspects of different embodiments are deemed described in combination with each other, wherein all combinations which can be deemed by a skilled person in the field as falling within the scope of the invention on the basis of reading of this document are included. These preferred embodiments are not limitative for the scope of protection of this document. The rights sought are defined in the appended claims.

The invention claimed is:

1. A method for performing of a location determination for determining of a candidate area of a heart disorder of a heart, while applying information from an ECG device and a processing unit, the method comprising:
    obtaining a torso model and/or a heart model of a subject;
    for the purpose of determining locations for positioning ECG electrodes on the subject, determining of an origin in the torso model and/or heart model;
    obtaining location information relating to a number of ECG electrodes to be positioned relative to the torso model and/or heart model of the subject;
    based on the obtained location information in the torso model and/or heart model, positioning of the number of ECG electrodes on the subject;
    obtaining of electrode measuring information related to respective distinct ECG electrodes,
    constructing weighted vectors based on electrode measuring information while applying a predetermined ECG feature,
    relating the weighted vectors to the origin and the respective electrodes;
    based on the weighted vectors relative to the origin, constructing an initial anatomical feature vector determining an initial anatomical feature geography and determining a direction towards the candidate area, wherein the initial anatomical feature geography is an initial ECG feature plane;
    constructing a further ECG feature vector based on shifting of the initial ECG feature plane to a position dividing the heart model; and
    repeating the constructing of the further ECG feature vector until the shifting is smaller than a predetermined threshold.

2. The method according to claim 1, wherein the anatomical feature geography is an activation front.

3. The method according to claim 1, wherein constructing of the weighted vectors based on electrode measuring information comprises relating of the electrode measuring information of an electrode vector with the predetermined ECG feature.

4. The method according to claim 1, wherein the heart disorder is a part of a muscle of the heart that is part of one or more walls of one or more ventricles of the heart.

5. The method according to claim 1, wherein the predetermined anatomical feature geography is an ECG feature geography.

6. The method according to claim 1, wherein the location information is obtained from an optical recording device.

7. The method according to claim 1, wherein the torso model and/or heart model of a subject is obtained from a scanning device.

8. The method according to claim 1, wherein the torso model and/or heart model of a subject is obtained from a database of models.

9. The method according to claim 1, wherein the origin is arranged in a proximity of a center of a bottom half of the heart.

10. The method according to claim 1, comprising analyzing a path of activation of premature ventricular contraction (PVC).

11. The method according to claim 10, comprising calculating of a number of activation sequences.

12. The method according to claim 11, comprising comparing of the path of activation or the activation sequences with the electrode measuring information.

13. The method according to claim 1 comprising outputting image data relating to the torso model and/or heart model to a graphical user interface for rendering on a display screen.

14. The method according to claim 1, comprising receiving instructions of a user.

15. The method according to claim 1, applied for at least one of the following: a further heart disorder, ventricular tachycardia, atrial tachycardia, chemical zones, Wolff-Parkinson-White syndrome, conductivity disorders, or any combination thereof.

16. The method according to claim 1, wherein the initial ECG feature plane is shifted in a direction of the further ECG feature vector.

17. The method according to claim 1, wherein constructing of the weighted vectors comprises integrating per electrodes of values of the predetermined ECG feature.

18. The method according to claim 1, wherein constructing of an initial ECG feature vector comprises summation of values of all of the weighted vectors.

19. The method according to claim 18, comprising:
    applying of an anatomical vector for matching of anatomical and/or isochrone vector with the initial or further ECG feature vector.

20. The method according to claim 1, comprising:
comparing of a predicted premature ventricular contraction (PVC) position with a position of successful ablation or stimulation.

21. The method according to claim 1, comprising providing information for representation thereof on a display screen for performing ablation of an area of the heart disorder; and rendering the information on the display screen.

22. The method according to claim 1, comprising:
assembling of output signals for controlling of a device for mechanically controlling thereof towards a position of an area in the heart;
based on a catheter signal, determining whether a tip of a catheter contacts a wall of the heart;
providing of an activation stimulus;
based on an ECG measurement related to the torso model and/or heart model, determining of a position of the tip of the catheter in the torso model and/or heart model;
determining whether the position sufficiently coincides with an intermediary point between a position on the wall of the heart where the stimulus was provided and a coordinate area of the heart disorder; and
assembling of controlling instructions for the device to this place the tip of the catheter towards the determined intermediary point.

23. The method according to claim 22, comprising determining the position of the tip of the catheter in the heart based on a local amplitude of a natural activation of the heart observed through the tip of the catheter.

24. A computer program product comprising a non-transitory computer readable medium having computer program code that, when executed on a processing unit, configures the processing unit to execute the method according to claim 1.

* * * * *